United States Patent [19]
Cozzi et al.

[11] Patent Number: 5,514,693
[45] Date of Patent: * May 7, 1996

[54] IMIDAZOLYL AND PYRIDYL DERIVATIVES OF PHENYL SUBSTITUTED 1,4-DIHYDROPYRIDINES AND PROCESS FOR THEIR PREPARATION

[75] Inventors: Paolo Cozzi; Germano Carganico; Mariia Menichincheri; Patricia Salvati, all of Milan, Italy

[73] Assignee: Farmitalia Carlo Erba S.r.l., Milan, Italy

[*] Notice: The portion of the term of this patent subsequent to Nov. 8, 2011, has been disclaimed.

[21] Appl. No.: 92,566

[22] Filed: Jul. 16, 1993

Related U.S. Application Data

[63] Continuation of Ser. No. 821,143, Jan. 16, 1992, abandoned, which is a continuation of Ser. No. 573,179, filed as PCT/EP89/01535, Dec. 14, 1989, abandoned.

[30] Foreign Application Priority Data

Dec. 15, 1988 [GB] United Kingdom ................... 8829292
Jul. 3, 1989 [GB] United Kingdom ................... 8915222

[51] Int. Cl.$^6$ ....................... A61K 31/44; C07D 401/10
[52] U.S. Cl. .................... 514/341; 514/332; 514/255; 514/318; 546/263; 546/278; 546/194; 544/365
[58] Field of Search .............................. 546/278; 514/341

[56] References Cited

U.S. PATENT DOCUMENTS

| | | | |
|---|---|---|---|
| 3,946,028 | 3/1976 | Bossert | 546/321 |
| 4,492,703 | 1/1985 | Goldmann | 546/139 |
| 4,599,341 | 7/1986 | Halczenko et al. | 546/39 |
| 4,766,213 | 8/1988 | Juraszyk et al. | 546/321 |

FOREIGN PATENT DOCUMENTS

| | | |
|---|---|---|
| 0088274 | 9/1983 | European Pat. Off. |
| 0215250 | 3/1987 | European Pat. Off. |
| 0245918 | 11/1987 | European Pat. Off. |

OTHER PUBLICATIONS

J. Med. Chem. 1993, 36, pp. 2964–2972, P. Cozzi, et al., "Imidazol-1-YL and Pyridin-3-YL Derivatives of 4-Phenyl-1,4-Dihydropyridines Combining CA2+ Antagonism and Thromboxane A2 Synthase Inhibition".

Poster Presentation, Oct. 1990, Congresso della Societa Italiana di Farmacologia, Taormina; "FCE 24265: UN Calcio Antagonista Inibitore Della Sintesi Del Trombossano"; F. Vaghi, et al.

8th Camerino–Noordwijkerhout Symposium, Camerino, 1991; "Imidazolyl And Pyridil Derivatives Of 1,4–Dihydropyridines Combining Ca–Antagonism And TxA$_2$ Synthase Inhibition"; P. Cozzi, et al.

Primary Examiner—Jane Fan
Attorney, Agent, or Firm—Oblon, Spivak, McClelland, Maier & Neustadt

[57] ABSTRACT

Imidazolyl and pyridyl derivatives of phenyl substituted 1,4-dihydropyridines of formula (I)

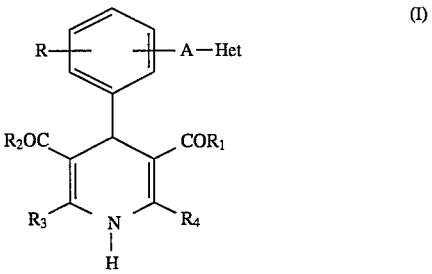

(I)

wherein Het is

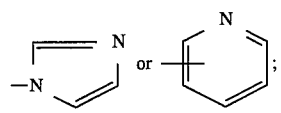

A represents a direct linkage, —$CH_2$—, $CH_2$—$CH_2$— or, when Het is

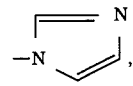

A may also represent —CH=CH—; R is hydrogen, halogen, $C_1$–$C_3$ alkyl or $C_1$–$C_3$ alkoxy; each of $R_3$ and $R_4$ is a $C_1$–$C_3$ alkyl group; one of $R_1$ and $R_2$ is a group —OR' wherein R' is a $C_1$–$C_6$ alkyl either unsubstituted or omega substituted by $C_1$–$C_3$ alkoxy or cyano, and the other is, independently, a) a group —OR";
b) a group

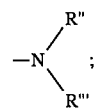

or c) a group —OR$^{IV}$ wherein R$^{IV}$ is hydrogen or a substituent selected from:
(i) —(CH$_2$)$_m$—CH=CH—Ph,

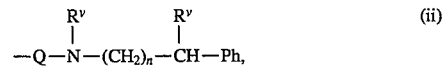
(ii)

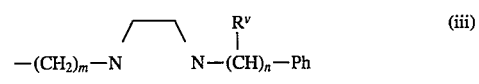

(iii)

and

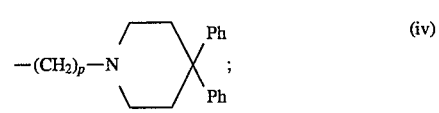
(iv)

are useful as Thromboxane A$_2$ (TxA$_2$) Synthase inhibitors and as calcium antagonists.

10 Claims, No Drawings

IMIDAZOLYL AND PYRIDYL DERIVATIVES OF PHENYL SUBSTITUTED 1,4-DIHYDROPYRIDINES AND PROCESS FOR THEIR PREPARATION

This application is a Continuation of application Ser. No. 07/821,143, filed Jan. 16, 1992, abandoned, which is a Continuation of application Ser. No. 07/573,179, filed Aug. 15, 1990, abandoned, which was filed as International Application No. PCT/EP89/01535 on Dec. 14, 1989.

The present invention relates to imidazolyl and pyridyl derivatives of phenyl substituted 1,4-dihydro-pyridines, to a process for their preparation and to pharmaceutical compositions containing them.

The imidazolyl and pyridyl derivatives of the present invention are compounds of the following formula (I)

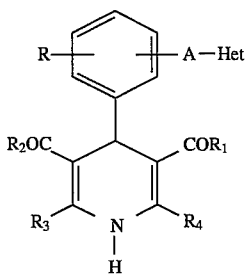

wherein Het is

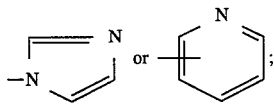

A represents a direct linkage, —$CH_2$—, —$CH_2$—$CH_2$— or, when Het is

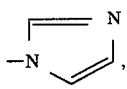

A may also represent —CH=CH—;

R is hydrogen, halogen, $C_1$-$C_3$ alkyl or $C_1$-$C_3$ alkoxy;
each of $R_3$ and $R_4$, which may be the same or different, is a $C_1$-$C_3$ alkyl group;
one of $R_1$ and $R_2$ is a group —OR' wherein R' is $C_1$-$C_6$ alkyl either unsubstituted or omega substituted by $C_1$-$C_3$alkoxy or cyano, and the other is, independently,
a) a group —OR' as defined hereabove; or
b) a group

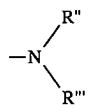

wherein each of R" and R'" which may be the same or different, is hydrogen or $C_1$-$C_3$ alkyl; or
c) a group —$OR^{IV}$ wherein $R^{IV}$ is hydrogen or a substituent selected from the group consisting of
(i) —$(CH_2)_m$—CH=CH—Ph, wherein m is an integer of 1 to 3 and Ph is a phenyl group either unsubstituted or substituted by one to three substituents chosen among $C_1$-$C_3$ alkyl, $C_1$-$C_3$alkoxy and halogen;

(ii)

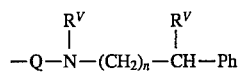

wherein Ph is as defined above;
Q is a $C_2$-$C_5$ alkylene radical; n is zero, 1 or 2; and each $R^V$ is, independently,
hydrogen, $C_1$-$C_3$ alkyl or Ph, wherein Ph is as defined above;

(iii)

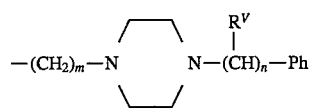

wherein m, n, $R^V$ and Ph are as defined above; and
(iv)

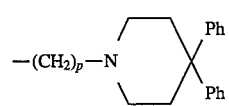

wherein p is 2 or 3 and Ph is as defined above.

The invention includes also the pharmaceutically acceptable salts of the compounds of formula (I) as well as all the possible isomers and stereoisomers thereof, and their mixtures.

Also the pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I), are included within the scope of the invention.

Pharmaceutically acceptable salts of the compounds of formula (I) are, especially, acid addition salts with inorganic, e.g. nitric, hydrochloric, hydrobromic, sulphuric, perchloric and phosphoric, acids, or organic e.g. acetic, propionic, glycolic, lactic, oxalic, malonic, malic, maleic, tartaric, citric, benzoic, cinnamic, mandelic, fumaric, methanesulfonic and salicylic acids.

Also the salts of the compounds of formula (I) with pharmaceutically acceptable bases, either inorganic bases, e.g. alkali metal, especially sodium or potassium, or alkaline-earth metal, especially calcium or magnesium hydroxides, or organic bases, e.g. alkylamines, preferably triethylamine, or basic naturally occurring aminoacids, preferably arginine, as well as the internal salts, i.e. zwitterions, are included within the scope of the present invention.

The alkyl and alkylene groups may be branched or straight chain groups.

A $C_1$-$C_3$ alkyl group is preferably methyl, ethyl or n-propyl.

A $C_1$-$C_6$ alkyl group is preferably a $C_1$-$C_4$ alkyl group, in particular methyl, ethyl, n-propyl, isopropyl or isobutyl.

A $C_1$-$C_3$ alkoxy group is, preferably, methoxy or ethoxy, particularly methoxy.

A $C_2$-$C_5$ alkylene group is, preferably, ethylene, 1,1'-dimethylethylene or a 1,1'- or 2,2'-dimethyl propylene radical.

A halogen is, preferably, chlorine, bromine or fluorine, in particular chlorine or fluorine.

When the substituent R is other than hydrogen, it is preferably located in position ortho in respect to the carbon atom of the phenyl ring which bears the 1,4-dihydro pyridine substituent.

In the group —OR' representing one or both the groups $R_1$ and $R_2$, R' is, preferably, unsubstituted $C_1$–$C_6$ alkyl, in particular methyl, ethyl or isopropyl.

When one of $R_1$ and $R_2$ is a group

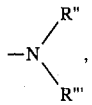

it is, preferably, —NH$_2$.

When one of $R_1$ and $R_2$ is a group —OR$^{IV}$ and R$^{IV}$ is a substituent as defined above under (i), (ii), (iii) or (iv), the group Ph therein preferably represents a phenyl group either unsubstituted or substituted by $C_1$–$C_3$ alkoxy, in particular methoxy, or halogen, in particular chlorine.

When R$^{IV}$ is a substituent as defined above under (ii) the $C_2$–$C_5$ alkylene Q radical therein is preferably 1,1'-dimethyl ethylene, 1,1'-dimethyl propylene or 2,2'-dimethyl propylene.

A representative example of a group-R$^{IV}$ as defined above under (i) may be the group

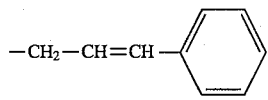

Representative examples of groups R$^{IV}$ as defined above under (ii) may be the following:

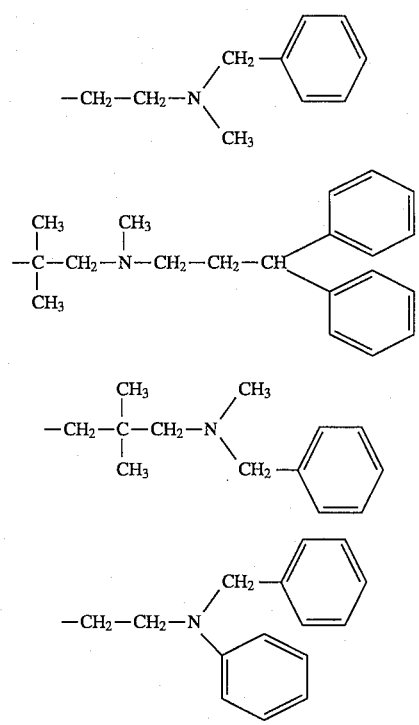

Representative examples of groups R$^{IV}$ as defined above under (iii) are the following:

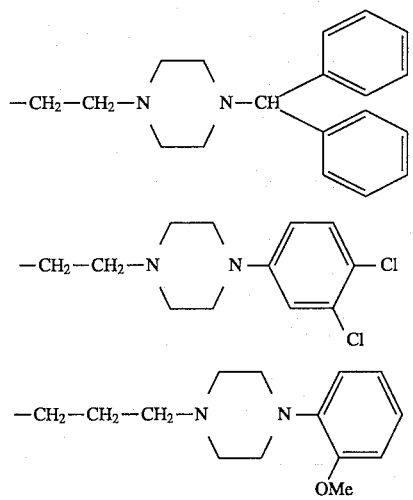

Representative example of a group R$^{IV}$ as defined above under (iv) is:

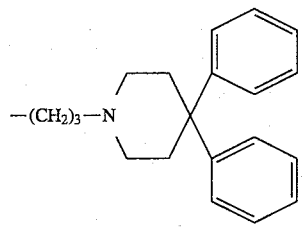

A preferred class of compounds according to the invention are the compounds of formula (I) wherein R is hydrogen, $R_3$ and $R_4$ are both methyl groups or both ethyl groups, and each of $R_1$ and $R_2$, which may be the same or different, is a group —OR' wherein R' is unsubstituted $C_1$–$C_6$ alkyl, and their pharmaceutically acceptable salts.

In the above preferred class the unsubstituted $C_1$–$C_6$ alkyl group representing R' is, preferably, $C_1$–$C_4$ alkyl, in particular methyl, ethyl or isopropyl.

Another preferred class of compounds according to the invention are the compounds of formula (I) wherein:

R is hydrogen;

$R_3$ and $R_4$ are both methyl groups or both ethyl groups; one of $R_1$ and $R_2$ is a group —OR' wherein R' is unsubstituted $C_1$–$C_6$ alkyl and the other is, independently, a group

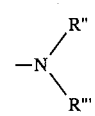

wherein R" and R'" are both hydrogen; or a group —OR$^{IV}$ wherein R$^{IV}$ is hydrogen or one of the groups (i) and (ii) defined above, and their pharmaceutically acceptable salts.

In the above preferred class the unsubstituted $C_1$–$C_6$ alkyl group for R' is, preferably, unsubstituted $C_1$–$C_4$ alkyl, in particular methyl, ethyl or isopropyl, and preferred values of the groups (i) and (ii) representing $R^{IV}$ are those previously indicated as representative examples.

When Het in the above formula (I) represents a pyridyl radical

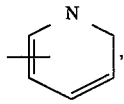

this is preferably substituted by the group A in position 3, that is meta to the pyridine nitrogen.

Specific examples of preferred compounds, according to the invention are:

1) 1,4-dihydro-2,6-dimethyl-4-[3-(1H-imidazol-1-yl)phenyl]-3,5-pyridinedicarboxylic acid, dimethyl ester;
2) 1,4-dihydro-2,6-dimethyl-4-[3-(1H-imidazol-1-yl)phenyl]-3,5-pyridinedicarboxylic acid, ethyl methyl ester;
3) 1,4-dihydro-2,6-dimethyl-4-[3-(1H-imidazol-1-yl)phenyl]-3,5-pyridinedicarboxylic acid, diethyl ester;
4) 1,4-dihydro-2,6-dimethyl-4-[3-(1H-imidazol-1-yl)phenyl]-3,5-pyridinedicarboxylic acid, isopropyl methyl ester;
5) 1,4-dihydro-2,6-dimethyl-4-[3-(1H-imidazol-1-yl)phenyl]-3,5-pyridinedicarboxylic acid, ethyl isopropyl ester;
6) 1,4-dihydro-2,6-dimethyl-4-[3-(1H-imidazol-1-yl)phenyl]-3,5-pyridinedicarboxylic acid, methyl 2-[methyl(phenylmethyl)amino]ethyl ester;
7) 1,4-dihydro-2,6-dimethyl-4-[3-(1H-imidazol-1-yl)phenyl]-3,5-pyridinedicarboxylic acid, ethyl 2-[methyl(phenylmethyl)amino]ethyl ester;
8) 1,4-dihydro-2,6-dimethyl-4-[2-(1H-imidazol-1-yl)phenyl]-3,5-pyridinedicarboxylic acid, dimethyl ester;
9) 1,4-dihydro-2,6-dimethyl-4-[2-(1H-imidazol-1-yl)phenyl]-3,5-pyridinedicarboxylic acid, diethyl ester;
10) 1,4-dihydro-2,6-dimethyl-4-[2-(1H-imidazol-1-yl)phenyl]-3,5-pyridinedicarboxylic acid, ethyl methyl ester;
11) 1,4-dihydro-2,6-dimethyl-4-[2-(1H-imidazol-1-yl)phenyl]-3,5-pyridinedicarboxylic acid, methyl 2-[methyl(phenylmethyl)amino]ethyl ester;
12) 1,4-dihydro-2,6-dimethyl-4-[3-(1H-imidazol-1-yl-methyl)phenyl]- 3,5-pyridinedicarboxylic acid, dimethyl ester;
13) 1,4-dihydro-2,6-dimethyl-4-[3-(1H-imidazol-1-yl-methyl)phenyl]- 3,5-pyridinedicarboxylic acid, diethyl ester;
14) 1,4-dihydro-2,6-dimethyl-4-[3-(1H-imidazol-1-yl-methyl)phenyl]- 3,5-pyridinedicarboxylic acid, isopropyl methyl ester;
15) 1,4-dihydro-2,6-dimethyl-4-[3-(1H-imidazol-1-yl-methyl)phenyl]- 3,5-pyridinedicarboxylic acid, methyl 2-[methyl(phenylmethyl)amino] ethyl ester;
16) 1,4-dihydro-2,6-dimethyl-4-[3-(1H-imidazol-1-yl-methyl)phenyl]- 3,5-pyridinedicarboxylic acid, ethyl 2-[methyl(phenylmethyl)amino] ethyl ester;
17) 1,4-dihydro-2,6-dimethyl-4-[2-(1H-imidazol-1-yl-methyl)phenyl]- 3,5-pyridinedicarboxylic acid, dimethyl ester;
18) 1,4-dihydro-2,6-dimethyl-4-[3-(2-(1H-imidazol-1-yl)ethenyl)phenyl]- 3,5-pyridinedicarboxylic acid, ethyl methyl ester;
19) 1,4-dihydro-2,6-dimethyl-4-[3-(2-(1H-imidazol-1-yl)ethenyl)phenyl]- 3,5-pyridinedicarboxylic acid, diethyl ester;
20) 1,4-dihydro-2,6-dimethyl-4-[3-(2-(1H-imidazol-1-yl)ethenyl)phenyl]- 3,5-pyridinedicarboxylic acid, methyl 2-[methyl(phenylmethyl)amino]ethyl ester;
21) 1,4-dihydro-2,6-dimethyl-4-[3-(1H-imidazol-1-yl)phenyl]-3,5-pyridinedicarboxylic acid, ethyl ester;
22) 1,4-dihydro-2,6-dimethyl-4-[3-(1H-imidazol-1-yl)phenyl]-3,5-pyridinedicarboxylic acid, 5-amide 3-ethyl ester;
23) 1,4-dihydro-2,6-dimethyl-4-[3-(1H-imidazol-1-yl-methyl)phenyl]- 3,5-pyridinedicarboxylic acid, ethyl ester;
24) 1,4-dihydro-2,6-dimethyl-4-[3-(2-(1H-imidazol-1-yl)ethenyl)phenyl]- 3,5-pyridinedicarboxylic acid, ethyl ester;
25) 1,4-dihydro-2,6-dimethyl-4-[3-(3-pyridyl)phenyl]-3,5-pyridinedicarboxylic acid, isobutyl methyl ester;
26) 1,4-dihydro-2,6-dimethyl-4-[3-(3-pyridyl)phenyl]-3,5-pyridinedicarboxylic acid, diethyl ester;
27) 1,4-dihydro-2,6-dimethyl-4-[3-(3-pyridyl)phenyl]-3,5-pyridinedicarboxylic acid, diisobutyl ester;
28) 1,4-dihydro-2,6-dimethyl-4-[3-(3-pyridyl)phenyl]-3,5-pyridinedicarboxylic acid, ethyl ester;
29) 1,4-dihydro-2,6-dimethyl-4-[3-(3-pyridyl)phenyl]-3,5-pyridinedicarboxylic acid, 5-amide-3-ethyl ester;
30) 1,4-dihydro-2,6-dimethyl-4-[3-(3-pyridyl)phenyl]-3,5-pyridinedicarboxylic acid, ethyl 2-[methyl(phenylmethyl)amino]ethyl ester;
31) 1,4-dihydro-2,6-dimethyl-4-[3-(3-pyridyl)phenyl]-3,5-pyridinedicarboxylic acid, isobutyl 2-[methyl(phenylmethyl)amino]ethyl ester;
32) 1,4-dihydro-2,6-dimethyl-4-[4-(3-pyridyl)phenyl]-3,5-pyridinedicarboxylic acid, diethyl ester;
33) 1,4-dihydro-2,6-dimethyl-4-[4-(3-pyridyl)phenyl]-3,5-pyridinedicarboxylic acid, ethyl ester;
34) 1,4-dihydro-2,6-dimethyl-4-[3-(3-pyridyl-methyl)phenyl]-3,5-pyridinedicarboxylic acid, diethyl ester;
35) 1,4-dihydro-2,6-dimethyl-4-[3-(3-pyridyl-methyl)phenyl]-3,5-pyridinedicarboxylic acid, ethyl ester;

The structural formulae of the compounds listed above, according to their progressive number, are reported in the following Table 1 which refers to compounds of formula (I) wherein R is hydrogen and $R_3$ and $R_4$ are both methyl groups.

TABLE 1

| No. | A | Position of A on phenyl ring | $R_1$ | $R_2$ | Het |
|---|---|---|---|---|---|
| 1 | direct linkage | meta | OMe | OMe | imidazol-1-yl |
| 2 | direct linkage | meta | OMe | OEt | imidazol-1-yl |

TABLE 1-continued

| No. | A | Position of A on phenyl ring | $R_1$ | $R_2$ | Het |
|---|---|---|---|---|---|
| 3 | direct linkage | meta | OEt | OEt | imidazol-1-yl |
| 4 | direct linkage | meta | OMe | OiPr | imidazol-1-yl |
| 5 | direct linkage | meta | OEt | OiPr | imidazol-1-yl |
| 6 | direct linkage | meta | OMe | OCH$_2$CH$_2$—N(Me)—CH$_2$—Ph | imidazol-1-yl |
| 7 | direct linkage | meta | OEt | OCH$_2$CH$_2$—N(Me)—CH$_2$—Ph | imidazol-1-yl |
| 8 | direct linkage | ortho | OMe | OMe | imidazol-1-yl |
| 9 | direct linkage | ortho | OEt | OEt | imidazol-1-yl |
| 10 | direct linkage | ortho | OMe | OEt | imidazol-1-yl |
| 11 | direct linkage | ortho | OMe | OCH$_2$CH$_2$—N(Me)—CH$_2$—Ph | imidazol-1-yl |
| 12 | CH$_2$ | meta | OMe | OMe | imidazol-1-yl |
| 13 | CH$_2$ | meta | OEt | OEt | imidazol-1-yl |
| 14 | CH$_2$ | meta | OMe | OiPr | imidazol-1-yl |
| 15 | CH$_2$ | meta | OMe | OCH$_2$CH$_2$—N(Me)—CH$_2$—Ph | imidazol-1-yl |
| 16 | CH$_2$ | meta | OEt | OCH$_2$CH$_2$—N(Me)—CH$_2$—Ph | imidazol-1-yl |
| 17 | CH$_2$ | ortho | OMe | OMe | imidazol-1-yl |
| 18 | CH=CH | meta | OMe | OEt | imidazol-1-yl |

TABLE 1-continued

| No. | A | Position of A on phenyl ring | R₁ | R₂ | Het |
|---|---|---|---|---|---|
| 19 | CH=CH | meta | OEt | OEt | 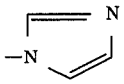 |
| 20 | CH=CH | meta | OMe | OCH₂CH₂—N(Bzl)(Me) | 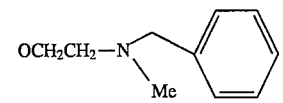 |
| 21 | direct linkage | meta | OEt | OH | 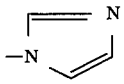 |
| 22 | direct linkage | meta | OEt | NH₂ | 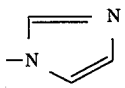 |
| 23 | CH₂ | meta | OEt | OH | 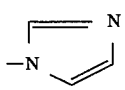 |
| 24 | CH=CH | meta | OEt | OH | 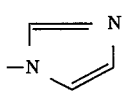 |
| 25 | direct linkage | meta | OMe | OiBu | 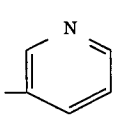 |
| 26 | direct linkage | meta | OEt | OEt | 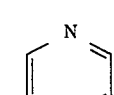 |
| 27 | direct linkage | meta | OiBu | OiBu | 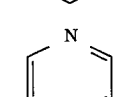 |
| 28 | direct linkage | meta | OEt | OH | 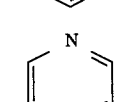 |
| 29 | direct linkage | meta | OEt | NH₂ | 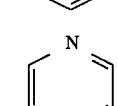 |
| 30 | direct linkage | meta | OEt | OCH₂CH₂—N(Bzl)(Me) | 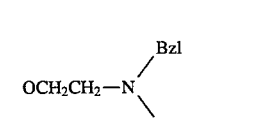 |
| 31 | direct linkage | meta | OiBu | OCH₂CH₂—N(Bzl)(Me) | 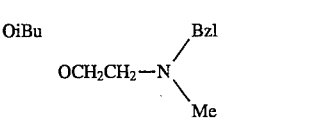 |
| 32 | direct linkage | para | OEt | OEt | 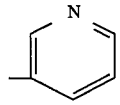 |

TABLE 1-continued

| No. | A | Position of A on phenyl ring | R₁ | R₂ | Het |
|---|---|---|---|---|---|
| 33 | direct linkage | para | OEt | OH | 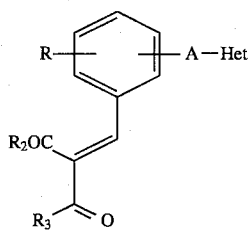 |
| 34 | CH₂ | meta | OEt | OEt | 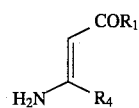 |
| 35 | CH₂ | meta | OEt | OH | 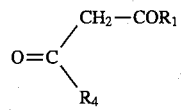 |

In Table 1 Me is methyl, Et is ethyl, iPr is isopropyl, iBu is isobutyl and Bzl is benzyl.

The compounds of the invention can be prepared by a process comprising:

a) reacting a compound of formula (II)

R—[phenyl]—A—Het
   |
   CH
   ‖
   C—OCR₂
   |
   R₃—C=O
(II)

wherein

R, A, Het, R₂ and R₃ are as defined above, but R₂ is different from —OH, with a compound of formula (III)

$$\begin{array}{c} COR_1 \\ \| \\ C \\ / \quad \backslash \\ H_2N \quad R_4 \end{array}$$ (III)

wherein

R₁ and R₄ are as defined above, but R₁ is different from —OH, thus obtaining a compound of formula (I) wherein R, A, Het, R₁, R₂, R₃ and R₄ are as defined above, with the exception of a compound of formula (I) wherein one of R₁ and R₂ is —OH; or b) reacting a compound of formula (II) with a compound of formula (IV)

$$\begin{array}{c} CH_2—COR_1 \\ / \\ O=C \\ \backslash \\ R_4 \end{array}$$ (IV)

wherein

R₁ and R₄ are as defined above, but R₁ is different from —OH, in the presence of an ammonium salt or hydroxide, thus obtaining a compound of formula (I) wherein R, A, Het, R₁, R₂, R₃ and R₄ are as defined above, with the exception of a compound of formula (I) wherein one of R₁ and R₂ is —OH; or c) reacting a compound of formula (V)

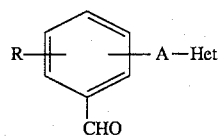

(V)

wherein

R, A and Het are as defined above, with a compound of formula (III) and a compound of formula (IV) together, thus obtaining a compound of formula (I) wherein R, A, Het, R₁, R₂, R₃ and R₄ are defined above, with the exception of a compound of formula (I) wherein one of R₁ and R₂ is —OH; or d) reacting a compound of formula (V) with a compound of formula (IV) wherein R₁ is a group —OR' as defined above in the presence of an ammonium salt or hydroxide, thus obtaining a compound of formula (I) wherein R, A, Het, R₃ and R₄ are as defined above and each of R₁ and R₂ is a group —OR' wherein R' is as defined above, and wherein R₁ is equal to R₂ and R₃ is equal to R₄; or e) transforming a compound of formula (I) wherein one of R₁ and R₂ is different from —OH into a corresponding compound of formula (I) wherein one of R₁ and R₂ is —OH;

and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of formula (I) into the single isomers.

The reactions described above under a), b), c), d), and e) can be performed by using known methods of the organic chemistry and, particularly, those typical of the chemistry of 1,4-dihydro-pyridines, such as those described e.g. by U. Eisner and J. Kuthan in Chem. Rev. 72, 1 (1972) and by D. M. Stout and A. I. Meyers in Chem. Rev. 82, 223, (1982).

In particular, reactions such as those described under a), b), c) and d) may be carried out following the same basic procedure, e.g. by heating the reactants at a temperature ranging from about 50° C. to about 150° C. in a suitable inert organic solvent such as, e.g. methanol, ethanol, isopropanol, dioxane, tetrahydrofuran, dimethylformamide, acetonitrile, dimethylsulfoxide, pyridine or their mixtures.

The ammonium hydroxide used in processes b) and d) may be, for example, in the form of concentrated aqueous ammonia, while an ammonium salt may be, for instance, ammonium acetate.

The transformation of process variant e) may be, for example, an acidic or alkaline hydrolysis of a compound of formula (I) wherein one of the $COR_1$ and $COR_2$ groups is a suitable labile ester group such as, e.g. a cyanoethyl or tert-butyl ester, the hydrolysis being performed, preferably at room temperature, following the usual procedures.

Optional conversions of a compound of formula (I) into another include, e.g. the following:

A compound of formula (I) containing a free carboxy group, may be converted into a compound of formula (I) containing an esterified carboxy group by esterification, e.g. via the corresponding acid halide, e.g. chloride, or reacting it with an excess of suitable aliphatic alcohol, or by direct esterification by means of acidic catalysis i.e. in the presence of dry HCl or $SOCl_2$ or $BF_3$-etherate.

A compound of formula (I) containing a free or esterified carboxy group may be converted in a compound of formula (I) containing a

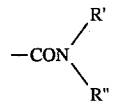

group, wherein R' and R" are as defined above, according to known methods.

For example, the conversion of an esterified carboxy group into the corresponding amide may be performed by direct reaction with ammonia or an appropriate amine in a suitable solvent, e.g. ether or benzene or using an excess of the amine as solvent, at temperatures ranging from room temperature to reflux. The conversion of a free carboxy group into the corresponding amides may be carried out via an intermediate reactive derivative which may be isolated or not.

Intermediate reactive derivatives may be active esters e.g. $NO_2$-phenyl esters, or N-hydroxysuccinimide esters, acid halides, preferably chloride, mixed anhydrides e.g. ethoxycarbonyl or tert-butylcarbonyl anhydrides, or the reactive intermediates obtained in situ by reaction of the acid with dicyclohexylcarbodiimide or carbonyldiimidazole.

The reactive intermediates, obtained following conventional ways, as those usually employed in the synthesis of peptides, are reacted with ammonia or an appropriate amine in a suitable solvent or with an excess of the amine itself at temperatures ranging preferably from about $-10°$ C. to about $50°$ C.

The optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans- isomers, may be carried out by fractional crystallization from a suitable solvent or by chromatography, either column chromatography or high pressure liquid chromatography.

Compounds of formula (II) may be prepared by reacting a compound of formula (V) with a compound of formula (IV) following the well known procedure for the Knoevenagel reaction, such as, e.g. described by G.Jones in Org. Reactions, 15 (1967) pp. 204–599.

Of course the meanings of $R_1$ and, respectively, $R_4$ in the compound (IV) must be those wanted for $R_2$ and, respectively, $R_3$ in the compound (II).

The process is preferably carried out by reacting compounds (IV) and (V) in the presence of a suitable base, e.g. diethylamine or pyridine, in a suitable solvent, e.g. ethanol or benzene, at temperatures ranging approximately from room temperature to the reflux.

Compounds of formula (III) and (IV) are known compounds or may be prepared following usual procedures from known compounds. Compounds of formula (V) are known compounds too or may be prepared by known methods from known compounds e.g. by reducing the corresponding alkyl esters of formula (VI)

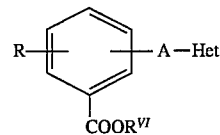

(VI)

wherein

R, A and Het are as defined above and $R^{VI}$ is $C_1-C_6$ alkyl.

The reduction may be performed in the presence of a suitable reducing agent as, e.g., diisobutylaluminium hydride in a suitable solvent such as, e.g., diethylether or tetrahydrofuran, at temperatures ranging from about $-80°$ C. to the room temperature.

Alternatively, compounds of formula (V) may be prepared by oxidation of the corresponding alcohol of formula (VII)

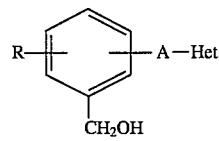

(VII)

wherein

R, A and Het are as defined above.

The process of oxidation may be performed following well known procedures for converting a primary alcohol to the corresponding aldehyde, e.g. those described by J. March in Advanced Organic Chemistry 1985, J. Wiley Publ., pp. 1057–1060.

Moreover compounds of formula (V) wherein A is a direct linkage, may be prepared by oxidation of compounds of formula (VIII)

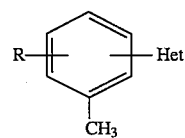

(VIII)

wherein

R and Het are as defined above.

The process of oxidation may be performed following known procedure, e.g. by use of chromic anhydride in acetic anhydride.

Compounds of formulae VI, VII and VIII are known compounds or may be prepared following known procedures, e.g. those reported in J. Med. Chem. (1981) 24, 1475 or in J. Med. Chem. (1981), 24, 1149 or in the European Patent Application 173172 A2.

In particular compounds of formulae (VI) and (VII) wherein Het is the imidazolyl radical

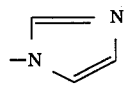

may be prepared, for example, by reacting imidazole or a salt thereof, e.g. the sodium salt, with, respectively, compounds of formula (IX) or of formula (X)

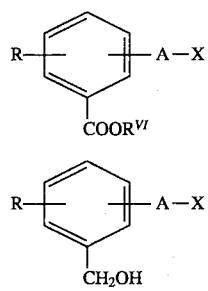

$$\text{(IX)}$$

$$\text{(X)}$$

wherein R, A and $R^{VI}$ are as defined above and X is a suitable leaving group, such as, for example, a suitable halogen, preferably chlorine or bromine, or a tosyl or a mesyl group, following experimental procedures well known from the chemical literature.

Compounds (IX) and (X) are known compounds.

The compounds of formula (I) of the present invention show, principally, inhibitory activity of Thromboxane $TxA_2$ Synthase and Calcium antagonistic activity.

Their ability to inhibit $TxA_2$ Synthase activity (as reflected by $TxB_2$ generated in whole blood during clotting or in isolated glomeruli) was tested in vitro and ex vivo in the rat. The in vitro experiments were carried out as follows:

The effect of the compounds on $TxA_2$ synthesis was evaluated in serum and in glomeruli isolated from kidney cortex of reduced renal mass rats (RRM). Ablation of >70% of renal mass in the rat results in hypertension, proteinuria and glomerular sclerosis of the remnant kidney. Rats with a remnant kidney have increased excretion of thromboxane in the urine when compared with normal rats [Purkerson et al. -Proc.Natl.Acad.Sci.USA 82, 193, 1985]. Blood was withdrawn from the abdominal aorta of the animals under light ether anesthesia. The blood was immediately divided in portions of 0.5 ml and distributed in glass tubes each containing a concentration of the test compounds or of the reference compounds, i.e. Dazoxiben, which is thromboxane synthase inhibitor [Randall et al. -Thromb.Res. 23, 145, 1981] and Acetylsalicylic acid (ASA), which is cyclooxygenase inhibitor.

Samples were then allowed to clot for 1 h at 37° C., centrifuged at 3000 rpm for 10 min, serum collected and stored at −20° C. until assayed. $TxB_2$ levels were determined by RIA according to previously described procedures [Patrono et al. -Thromb.Res. 17, 3/4,317, 1980] using highly specific antibody.

The isolation of glomeruli was performed as previously described [Patrignani et al., -J.Pharm. Exp. Ther. 228, 2, 472, 1984].

The isolated glomeruli of 4 rats were pooled, suspended in modified Krebs buffer (pH 7.3) and divided into portions of 1 ml each containing a concentration of the test compounds or of the reference compounds.

The $TxA_2$ synthesis was induced by incubating the glomeruli under shaking at 37° C. for 1 h. At that time the incubation was stopped by centrifugation at +4° C., the supernatant collected and stored at −20° C. until assayed by RIA.

The ex vivo experiments were performed as follows.

The compounds were orally administered to RRM rats by gavage at the dose of 2.5 mg/kg in 0.5% methocel. One hour after treatment rats were anaesthetised with ether, blood was withdrawn from the abdominal aorta and allowed to clot for 1 h at 37° C. Samples were then centrifuged, serum collected and stored at −20° C. until assayed.

The compounds of the invention showed remarkable activity in both the in vitro and the ex vivo tests.

In particular, for example, the compounds of the invention 1,4-dihydro-2,6-dimethyl-4-[3-(1H-imidazol-1-yl)-phenyl]-3,5-pyridine dicarboxylic acid, diethyl ester (internal code FCE 24265) and 1,4-dihydro-2,6-dimethyl-4-(3-(3-pyridyl)phenyl)-3,5-pyridine dicarboxylic acid, diethyl ester (internal code FCE 26055) were found to exhibit a marked inhibitory activity on $TxA_2$ synthesis in whole blood being 7 and, respectively, 3 times more potent than the reference compound Dazoxiben, and being 247 and, respectively, 90 times more potent than the reference compound ASA.

The results are summarized in Table 1.

Table 1: In vitro effect on $TxB_2$ synthesis in RRM rats whole blood.

Data are expressed as $IC_{50}$ (M) and limits for $P=0.95$

| Drug | Whole blood |
| --- | --- |
| FCE 24265 | $1.7 \times 10^{-7}$ |
| | $(1.1 \times 10^{-7} - 2.4 \times 10^{-7})$ |
| FCE 26055 | $4.5 \times 10^{-7}$ |
| | $(2.02 \times 10^{-7} - 9.1 \times 10^{-7})$ |
| DAZOXIBEN | $1.2 \times 10^{-6}$ |
| | $(6.8 \times 10^{-7} - 1.9 \times 10^{-6})$ |
| ASA | $4.2 \times 10^{-5}$ |
| | $(3.1 \times 10^{-5} - 5.6 \times 10^{-5})$ |

Moreover the compounds of the invention were also active in inhibiting glomerular $TxB_2$ production.

In particular, for example, the compound 1,4-dihydro-2,6-dimethyl-4-[3-(1H-imidazol-1-yl)-phenyl]-3,5-pyridinedicarboxylic acid, diethyl ester (FCE 24265) was shown to be 4.7 and, approximately, 4,000 times more potent than Dazoxiben and ASA, respectively, on glomerular $TxB_2$ synthesis.

These results are summarized in Table 2.

Table 2: In vitro effect on $TxB_2$ synthesis in RRM rats glomeruli.

Data are expressed as $IC_{50}$ (M) and limits for $P=0.95$

| Drug | Glomeruli |
| --- | --- |
| FCE 24265 | $3.6 \times 10^{-8}$ |
| | $(2.9 \times 10^{-8} - 4.8 \times 10^{-8})$ |
| Dazoxiben | $1.7 \times 10^{-7}$ |
| | $(1.2 \times 10^{-7} - 2.2 \times 10^{-7})$ |
| ASA | $1.4 \times 10^{-4}$ |
| | $1.1 \times 10^{-4} - 1.7 \times 10^{-4}$ |

In the ex vivo test in the rat the same compound FCE 24265 was found to inhibit the synthesis of $TxA_2$ with an $ED_{50}$ value of 2.3 mg/kg p.o.

The Calcium antagonistic activity of the compounds of the invention was tested by evaluating their effect on the response of the isolated guinea pig ileum to contractions of $K^+$ in vitro.

The terminal ileum of albine male guinea pigs (250–300 b.w) was immediately removed when the animal were killed, washed and maintained in a 10 ml organ bath containing Tyrode's solution gassed with 95% $O_2$ and 5% $CO_2$ and thermoregulated at 37° C.

The tissue was preloaded with 1 g and contractions were recorded by a Basile DY1 isometric transducer on a Watanabe Mark V recorder. Contractions to $K^+$60 mM were obtained at a 15 min intervals in absence and presence of increasing concentrations of test compounds. The antagonists potencies were expressed as $IC_{50}$ values, i.e. the molar concentration of antagonist which inhibits $K^+$ response by 50%.

The compounds of formula (I) showed remarkable activity also in this test. For example, in particular, the compounds of the invention 1,4-dihydro-2,6-dimethyl-4-[3-(1H-imidazol-1-yl)-phenyl]- 3,5-pyridine dicarboxylic acid, diethyl ester (FCE 24265), 1,4-dihydro-2,6-dimethyl-4-(3-(3-pyridyl)phenyl)- 3,5-pyridine dicarboxylic acid (2-(N-benzyl-methylamino)ethyl)-ethyl ester (FCE 26225) and 1,4-dihydro-2,6-dimethyl-4-[3-(3-pyridyl)phenyl]-3,5-pyridine dicarboxylic acid, diethyl ester (FCE 26055) at concentrations from $3 \times 10^{-8}$M to $1 \times 10^{-6}$M were found to inhibit dose-dependently $K^+$ contractions with $IC_{50}$ value of $6.2 \times 10^{-8}$M, $6.4 \times 10^{-8}$M and $1.1 \times 10^{-7}$M respectively.

The compounds of the invention, being able to inhibit selectively the formation of $TxA_2$ can be used as vasodilatory and antiaggregant agents, for example in all the cases of thrombosis, periferal vasculopaties and coronary artery disease. In fact inhibition of $TxA_2$ production reduces the probability of thrombi formation and of vasoconstriction with consequent ischemic events and, leaving unaltered (or increasing) $PGI_2$ production, improves vasodilation, tissue blood supplies and protects the vessel wall.

Another use of the compounds of the invention is for the treatment of migraine. As is known, for example, in the case of migraine it has been demonstrated a diffused vasoconstriction induced by platelet $TxA_2$ overproduction [J.Clin. Pathol. (1971), 24, 250; J. Headache (1977) 17, 101].

A platelet overproduction of $TxA_2$ and MDA (malondialdehyde) in diabetes mellitus has been demonstrated and correlated with microcirculatory defects in the illness [Metabolism (1979) 28, 394; Eu.J.Clin.Invest. (1979) 9, 223; Thrombosis Haemost. (1979), 42, 983; J.Lab.Clin.Med. (1981) 97, 87].

Therefore, the compounds of the invention can be used, e.g., in the treatment of diabetic microangiopathy.

Moreover, the compounds of the invention can be used as anti-inflammatory agents. As is known, for example, fluid obtained from carrageenin-induced granuloma converts arachidonic acid into $TxA_2$ in vitro and $TxA_2$ levels are increased in the synovial fluid of rheumatoid arthritis patients and in the fluid of carrageenin-induced inflammation in rats [Prostaglandins (1977), 13, 17; Scand. J.Rheum. (1977), 6 151].

Moreover the compounds of the invention can be used as hypotensive agents.

Recently it has been in fact demonstrated that an overproduction of $TxA_2$ is involved in the pathogenesis of hypertension and that a specific inhibitor of $TxA_2$ production may be employed in hypertension [Eu.J.Pharmacol. (1981), 70, 247].

An increased $TxA_2$ synthesis and decreased prostacyclin synthesis are also reported in pregnancy-induced hypertension [Am.J.Obstet:Gynecol. (1987), 157, 325; Hypertension (1988), 11, 550]. Treatment with thromboxane synthase inhibitors is therefore useful in this pathology.

The antihypertensive activity of the compounds of the invention was tested in chronically cannulated hypertensive rats (SHR).

For intra-arterial measurements of blood pressure (MBP) catheters (PE50 Clay Adams) were implanted in the right carotid artery under alothane anesthesia. Two days after surgery the animals were placed in a Ballman cage and the arterial catheter was connected to a stathman P23 Db pressure transducer and a Beckman multichannel R611 BP recorder for continuous monitoring of MBP and heart rate (HR).

Measurements were made predrug and 0.5, 1, 2, 4, 6 h after drug or vehicle (methocel 0.5% w/v).

In the above test the compounds of the invention were found to be active. For example, the compound of the invention FCE 24265 exhibited a marked antihypertensive activity with a rapid onset, the peak effect (−30±4 mm Hg) being reached at 30 minutes postdrug. Blood pressure returned toward normal levels 3 hours after treatment. No changes in heart rate were observed.

Furthermore it has been shown a role of $TxA_2$ in the pathogenesis of ulcerative disorders of the stomach in accordance with its powerful gastric vasoconstrictory activity, so that also in this field a $TxA_2$ inhibitor is useful [Nature (1981), 202, 472]. In fact the compounds of the invention are indicated for the treatment of peptic ulcers.

The compounds of the invention can be also antitumoral agents. It is known, for example, that a selective inhibition of $TxA_2$ synthesis has been demonstrated to reduce the number of lung metastases and to slow down tumor growth [Nature (1982), 295, 188].

In view of the correlation between $TxA_2$ synthesis and calcium transport, recently showed by some authors, specific $TxA_2$ synthetase inhibitors, such as the compounds of the invention, can also find use in the treatment of osteoporosis, e.g. post-menopausal osteoporosis [Prostaglandins (1981), 21, 401].

Moreover the compounds of the invention are indicated for the treatment of angina pectoris.

In this respect, it is known, for example, that high levels of $TxB_2$ have been found in patients with Prinz-metal's angina [Prostaglandins and Med. (1979), 2, 243] and in patients with recurrent angina attacks [Sixth Intern. Congress on Thrombosis, Monte Carlo October. 1980 Abs N° 140].

The platelet antiaggregatory activity of the compounds of the invention was evaluated in vitro and in vivo, for example, according to the modified methods of Born [Born G. V. R., Nature 194, 927 (1962)] and Silver [Silver M. J., Science 183, 1085 (1974)].

The compounds of this invention were found in vitro to have inhibitory activity on platelet aggregation induced by collagen in human platelet rich plasma.

Therefore the compounds of the invention may be useful in preventing or reducing platelet loss during extracorporeal circulation; for example during coronary artery by-pass and graft procedures or during kidney dialysis.

It has been moreover shown that circulatory shock, for example endotoxic and haemorragic shock, is associated with increased $TxA_2$ synthesis so that the compounds of the invention can be useful in these pathologies. Moreover, the compounds of the present invention can also be useful for the treatment of bronchial hyperreactivity in the therapy of asthma.

A role for $TxA_2$ in asthma can be inferred on the basis of its bronchoconstrictory activity in experimental animal models [Br. J. Pharmacol. (1984), 82 (3) 565]. An inhibitory activity of bronchospasm induced by Platelet Activating Factor (PAF) in rats is also reported, e.g. for the $TxA_2$ synthetase inhibitors described in British Patent No. 2205494.

The compounds of the present invention can also find use in the treatment of nephropathies, e.g. forms of glomerulonephritis, diabetic nephropathy or nephropathies secondary to systemic lupus erithematous (SLE), and in the prevention and/or treatment of Cyclosporin A- induced nephrosis.

Recently a positive correlation between enhanced intrarenal synthesis of $TxA_2$ and the progression of chronic glomerular disease has been demonstrated in different animal models of immune and non-immune renal damage and in humans [J. Clin. Invest. (1985) 75, 94; J. Clin. Invest. (1985), 76, 1011].

The compounds of the invention may be also used to inhibit the renal and cardiac transplant rejection. In fact after transplantation increased urinary $TxB_2$ excretion or whole blood $TxA_2$ synthesis have been reported both in man and rats [Lancet (1981), ii, 431; Transplantation (1987) 43, 346].

Another use of the compounds of the present invention is in the treatment of hyperlipidaemia, namely hypercholesterolaemia and hypertriglyceridaemia secondary to nephrotic syndrome.

Hyperlipidaemia is a common feature of nephrotic syndrome in man [New Engl. J. Med. (1983) 312 (24) 1544] and in addition elevated triglycerides and cholesterol levels are reported in animal models such as doxorubicin induced nephrotic syndrome [Expt. Mol. Pathology (1983), 39, 282]; elevated urinary albumin excretion has been suggested as the pathogenetic mechanism [Kidney international (1987), 32, 813].

It has also been shown that in cholesterol fed rabbit, an animal model of diet induced atherosclerosis, arachidonic acid metabolism is an important factor in early lesion development. In particular a shift in metabolism from $TxA_2$ to $PGE_2$ may suppress lesion development (i.e. atheromatous plaque) in hypercholesterolaemia.

The compounds of the invention can also be used in association with thrombolytic agents (e.g. tPA, Streptokinase, pro-Urokinase) in order to reduce the dose of the latter required in thrombolytic therapy, and to lower the incidence of reocclusion and possibly haemorrhage.

Furthermore, in view of their Calcium antagonistic activity (slow inward Calcium channel blockers; Calcium entry blockers), by reducing the Calcium influx across the membrane of the excitable heart muscle cells or the coronary and systemic arterial smooth muscle cells, the compounds of the invention may be useful to control the myocardial, coronary and peripheral arterial contractility.

Due to this activity their use in the treatment of hypertension, angina, tachicardias and myocardial arrhythmias, cerebral ischemia and migraine is further supported. Moreover, acting on the Calcium accumulation in the arterial vessel wall occurring in the development of the atheroma, and also in view of their platelet aggregation inhibitory effect,they may have useful application as antiatherosclerotic agents.

More particularly, due to the dual activity as $TxA_2$ Synthase inhibitors and Calcium-antagonists, the compounds of the invention may exert a synergistic beneficial effect in those pathological conditions, in which the vasoconstriction is the results of multiple mechanism and is associated with enhanced $TxA_2$ biosynthesis.

Thus the compounds of the invention can be particularly useful in the prevention and in the treatment of pathologies such as, for example, hypertension, unstable angina, cerebral ischemia, migraine, progressive glomerulosclerosis and atherosclerosis.

The toxicity of the compounds of the invention is negligible, so that they can be safely used in therapy.

Mice and rats which had been deprived of food for nine hours were treated orally with single administrations of increasing doses of compounds of the invention, then housed and normally fed. For example the orientative acute toxicity ($LD_{50}$) of the compound FCE 24265, assessed on the seventh day after treatment, was higher than 800 mg/kg.

In view of their high therapeutic index the compounds of the invention can be safely used in medicine.

The therapeutic regimen for the different clinical syndromes must be adapted to the type of pathology taking into account, as usual, also the route of administration, the form in which the compound is administered and the age, weight and conditions of the subject involved.

The oral route is suitable, in general, for all conditions requiring such compounds. Preference is given to intravenous injection or infusion for the treatment of acute pathological states.

For maintenance regimens the oral or parenteral, e.g. intramuscular, route is preferred.

The dosage level suitable for oral administration to adult humans of the compounds of the invention, e.g. of 1,4-dihydro-2,6-dimethyl- 4-[3-(1H-imidazol-1-yl)phenyl]-3,5-pyridine dicarboxylic acid, diethyl ester and 1,4-dihydro-2,6-dimethyl-4-[3-(3-pyridyl)phenyl]-3,5-pyridine dicarboxylic acid, diethyl ester may range from about 5 mg to about 500 mg per dose 1 to 3 times a day, preferably from about 20 mg to about 150 mg per dose 1 to 3 times a day.

Of course, these dosage regimens may be adjusted to provide the optimal therapeutic response.

As already said, the present invention includes in its scope also the pharmaceutical compositions containing the compounds of formula (I) in association with pharmaceutically acceptable carriers or diluents.

The nature of the pharmaceutical compositions will, of course, depend upon the desired route of administration.

The compositions may be formulated In the conventional manner with the usual ingredients. For example, the compounds of the invention may be administered in the form of aqueous or oily solutions or suspensions, tablets, pills, capsules, syrups, drops or suppositories.

Thus, for oral administration, the pharmaceutical compositions containing the compounds of this invention are preferably sugar or film coated tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpirrolidone; disaggregating agents, such as starches, alginic acid, alginates, sodium starch glycolate; effervescing mixtures: dyestuffs; sweeteners; wetting agents, such as lecithin, polysorbates, lauryl-sulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be, e.g., syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as a carrier, for example, sterile water or, preferably, they may be in the form of sterile aqueous isotonic saline solutions.

The suppositories may contain, together with the active compound, a pharmaceutically acceptable carrier e.g. cocoa-butter, polyethylene glycol, a polyoxyethylene sorbitan fatty acid ester surfactant or lecithin.

In this specification the abbreviations "OMe", "OEt", "OiPr", "Et$_2$O", "AcOH" stand, respectively, for "methoxy", "ethoxy", "isopropoxy", "diethyl ether", "acetic acid". The following examples illustrate but do not limit the present invention.

EXAMPLE 1

A mixture of 17.2 g (0.1 mol) of 3-(1H-imidazol-1-yl)-benzaldehyde, 26 g (0.2 mol) of ethyl acetoacetate and 5 ml of concentrated NH$_4$OH in absolute ethanol (25 ml) was refluxed for 6 hours. The mixture was poured into 500 ml of ice-water and the aqueous solution was extracted with methylene chloride. The organic layers were put together, dried over CaCl$_2$ and evaporated under vacuum. The crude product was recrystallized from Et$_2$O, giving 25.7 g (65%) of 1,4-dihydro-2,6-dimethyl-4-[3-(1H-imidazol-1-yl)phenyl]-3,5-pyridinedicarboxylic acid, diethyl ester, m.p. 202°–204° C.;

Elemental analysis: Found: C 66.83; H 6.38; N 10.62 Calculated for C$_{22}$H$_{25}$N$_3$O$_4$: C 66.81; H 6.37; N 10.62

TLC: eluant CHCl$_3$/CH$_3$OH/AcOH=90/10/1, R$_f$=0.53
N.M.R. (CDCl$_3$) δ p.p.m.: 1.23 (6H,t, CH$_2$C$\underline{H}_3$) 2.38 (6H, s,=C—C$\underline{H}_3$) 4.12 (4H,q,C$\underline{H}_2$ CH$_3$) 5.08 (1H,s,CH at 4 position of dihydropyridine) 6.27 (1H,br s,NH) 7.1–7.4 (6H,m,phenylic+CH=CH imidazolic protons) 7.82 (1H,br s,N—C$\underline{H}$—N).

The intermediate 3-(1H-imidazol-1-yl)-benzaldehyde was prepared by reducing with diisobutylaluminium hydride the corresponding ethyl ester (m.p. 76°–78° C., from Et$_2$O), obtained in turn from the free corresponding benzoic acid.

The latter, namely 3-(1H-imidazol-1-yl)-benzoic acid, was obtained from 3-bromobenzoic acid by reaction with imidazole in refluxing nitrobenzene, in the presence of K$_2$CO$_3$ and CuBr. By proceeding analogously the following compounds may be prepared:

1,4-dihydro-2,6-dimethyl-4-[3-(1H-imidazol-1-yl-methyl)phenyl]-3,5-pyridinedicarboxylic acid, diethyl ester, m.p. 196°–199° C.;

Elemental analysis: Found: C 67.15; H 6.64; N 10.11 Calculated for C$_{23}$H27N$_3$O$_4$: C 67.46; H 6.65; N 10.26

TLC: eluant CHCl$_3$/CH$_3$OH=92/8, R$_f$=0.57
N.M.R. (CDCl$_3$) δ p.p.m.: 1.21 (6H,t,CH$_2$C$\underline{H}_3$) 2.30 (6H,s,=C—CH$_3$) 4.08 (4H,q,C$\underline{H}_2$CH$_3$) 4.98 (1H,s,CH at 4 position of dihydropyridine) 5.09 (2H,s,=C—C$\underline{H}_2$—N) 5.77 (1H,s,NH) 6.8–7.7 (7H,m,phenylic+CH=CH imidazolic protons)

1,4-dihydro-2,6-dimethyl-4-[3-(1H-imidazol-1-yl)phenyl]-3,5-pyridinedicarboxylic acid, dimethyl ester, m.p. 212°–216° C.;

Elemental analysis: Found: C 65.11; H 5.78; N 11.31 Calculated for C$_{20}$H$_{21}$N$_3$O$_4$: C 65.38; H 5.76; N 11.44

TLC: eluant CHCl$_3$/CH$_3$OH=95/5 R$_f$=0.28
N.M.R. (CDCl$_3$) δ p.p.m.: 2.43 (6H,s,=C—C$\underline{H}_3$) 3.71 (6H,s,COOC$\underline{H}_3$) 5.17 (1H,s,CH at 4 position of dihydropyridine) 5.80 (1H,s,NH) 7.1–7.5 (6H,m,phenylic+CH=CH imidazolic protons) 7.9 (1H,br s,N—C$\underline{H}$—N);

1,4-dihydro-2,6-dimethyl-4-[2-(1H-imidazol-1-yl)phenyl]-3,5-pyridinedicarboxylic acid, diethyl ester, m.p. 208°–210° C.

Elemental analysis: Calculated for C$_{22}$H$_{25}$N$_3$O$_4$: C 66.81; H 6.31; N 10.62 Found C 66.12; H 6.30; N 10.50

T.L.C.: eluant CHCl$_3$/CH$_3$OH=90/10, Rf=0.57;

1,4-dihydro-2,6-diethyl-4-[3-(1H-imidazol-1-yl)phenyl]-3,5-pyridinedicarboxylic acid, diethyl ester, m.p. 171°–172° C.;

Elemental analysis: Calculated for C$_{24}$H$_{29}$N$_3$O$_4$: C 68.06;H 6.90;N 9.92 Found C 67.80; H 6.90; N 9.81

T.L.C.: eluant CHCl$_3$/CH$_3$OH=180/20, Rf=0.66
N.M.R. (CDCl$_3$) δ p.p.m.: 1.21 (12H,m,2 CO$_2$CH$_2$C$\underline{H}_3$+2 =C—CH$_2$C$\underline{H}_3$) 2.63 (2H, dq,2 =C—C $\underline{H}\underline{H}_A$H$_B$CH$_3$) 2.88 (2H,dq,2 =C—CH$_A$$\underline{H}_B$CH$_3$) 4.10 (4H, m,2 CO$_2$C$\underline{H}_2$CH$_3$) 5.06 (1H,s,C$\underline{H}$ at 4 position of dihydropyridine) 6.12 (1H,bs,N$\underline{H}$) 7.10–7.40 (6H,m,C$\underline{H}$ at 2,4,5,6 positions of phenyl ring and C$\underline{H}$ at 4,5 positions of imidazole) 7.95 (1H,s,C$\underline{H}$ at 2 position of imidazole);

1,4-dihydro-2,6-dimethyl-4-[2-methyl-5-(imidazol-1-yl) phenyl]-3,5-pyridinedicarboxylic acid, diethyl ester, Elemental analysis: Found: C 65.97; H 6.58; N 10.08; Calculated for C$_{23}$H$_{27}$N$_3$O$_4$: C 67.46; H 6.65; N 10.26

NMR (CDCl$_3$) δ p.p.m: 1.23 (6H,t,2CO$_2$CH$_2$C$\underline{H}_3$) 2.37 (6H,s,2 =C—C$\underline{H}_3$) 2.66 (3H,s,C$\underline{H}_3$ at 2 position of phenyl ring) 4.14 (4H,q,2CO$_2$C$\underline{H}_2$CH$_3$) 5.22 (1H,s,C$\underline{H}$ at 4 position of dihydropyridine) 6.36 (1H,s,N$\underline{H}$) 7.00–7.50 (5H,m,C$\underline{H}$ at 3,4,6 positions of phenyl ring and at 4,5 positions of imidazole) 8.15 (1H,s,C$\underline{H}$ at 2 position of imidazole)
MS: m/z 409 M$^+$;

1,4-dihydro-2,6-dimethyl-4-[2-fluoro-3-(imidazol-1-yl)phenyl]-3,5-pyridinedicarboxylic acid, diethyl ester;

1,4-dihydro-2,6-dimethyl-4-[2-(1H-imidazol-1-yl)phenyl]-3,5-pyridinedicarboxylic acid, dimethyl ester;

1,4-dihydro-2,6-dimethyl-4-[3-(1H-imidazol-1-yl-methyl)phenyl]- 3,5-pyridinedicarboxylic acid, dimethyl ester;

1,4-dihydro-2,6-dimethyl-4-[2-(1H-imidazol-1-yl-methyl)phenyl]- 3,5-pyridinedicarboxylic acid, dimethyl ester; and 1,4-dihydro-2,6-dimethyl-4-[3-(2-(1H-imidazol-1-yl)methyl)phenyl]- 3,5-pyridinedicarboxylic acid, diethyl ester.

EXAMPLE 2

A mixture of 0.27 g (1.56 mmol) of 3-(1H-imidazol-1-yl)benzaldehyde, 0.204 g (1.56 mmol) of ethyl acetoacetate and 0.18 g (1.56 mmol) of methyl-3-aminocrotonate in absolute ethanol (10 ml) was refluxed for 6 hours.

The mixture was poured into 20 ml of ice-water and the aqueous solution was extracted with methylene chloride.

The organic layers were put together, dried over CaCl$_2$ and evaporated under vacuum. The crude product was purified over flash silica-gel column (ethyl acetate: n-hexane=1:4), giving 0.36 g (60%) of 1,4-dihydro-2,6-dimethyl-4-[3-(1H-imidazol-1-yl)phenyl]-3,5-pyridinedicarboxylic acid, ethyl methyl ester, m.p. 197°–200° C.;

Elemental analysis: Found: C 65.57; H 6.20; N 10.79 Calculated for C$_{21}$H$_{23}$ N$_3$O$_4$: C 66.13; H 6.08; N 11.02

TLC: eluant CHCl$_3$/CH$_3$OH=90/10, R$_f$=0.64
N.M.R. (DMSO-d$_6$) δ p.p.m.: 1.10 (3H,t,CH$_2$C$\underline{H}_3$) 2.28 (6H,s,=C—C$\underline{H}_3$) 3.57 (3H,s,COOC$\underline{H}_3$) 4.01 (2H,q,C $\underline{H}_2$CH$_3$) 4.93 (1H,s,CH at 4 position of dihydropyridine) 7.05–7.6 (6H,m,phenylic+CH=CH imidazolic protons) 8.09 (1H,dd,N—C$\underline{H}$—N) 8.88 (1H,s,NH).

By proceeding analogously the following compounds may be prepared:

1,4-dihydro-2,6-dimethyl-4-[3-1H-imidazol-1-yl)phenyl]-3, 5-pyridinedicarboxylic acid, 2-cyanoethyl ethyl ester, Elemental analysis: Found: C 65.38; H 5.73; N 13.15 Calculated for C$_{23}$H$_{24}$N$_4$O$_4$: C 65.70; H 5.75; N 13.32

N.M.R. (DMSO-d$_6$) δ p.p.m.: 1.10 (3H,t,CH$_2$C$\underline{H}_3$) 2.28 (6H,s,=C—C$\underline{H}_3$) 2.58 (2H,t, COOCH$_2$C$\underline{H}_2$CN) 4.01 (2H, q,C$\underline{H}_2$CH$_3$) 4.05 (2H,t,COOC$\underline{H}_2$CH$_2$CN) 4.93 (1H,s,CH at 4 position of dihydropyridine) 7.05–7.6 (6H,m,phenylic+ CH=CH imidazolic protons) 8.09 (1H,dd,N—C$\underline{H}$—N) 8.88 (1H,s,NH);

1,4 dihydro-2,6-dimethyl-4-[3-(1H-imidazol-1-yl)phenyl]-3,5-pyridinedicarboxylic acid, ethyl 2-[methyl(phenylmethyl)amino] ethyl ester, Elemental analysis: Calculated for: $C_{30}H_{34}N_4O_4$: C 70.02; H 6.66; N 10.89 Found: C 69.17; H 6.72; N 10.72

T.L.C.: eluant $CHCl_3/CH_3OH=95/5$, $R_f=0.34$

N.M.R. ($CDCl_3$) δ p.p.m.: 1.22 (3H,t,$CO_2CH_2C\underline{H}_3$) 2.20 (3H,s,N($C\underline{H}_3$) ($CH_2Ph$)) 2.37 (6H,s,2 =C—$CH_3$) 2.69 (2H, t,$C\underline{H}_2N(CH_3)$ ($CH_2Ph$)) 3.50 (2H,s,N($CH_3$) ($CH_2Ph$)) 4.11 (2H,q,$CO_2C\underline{H}_2CH_3$) 4.21 (2H,t,$CO_2C\underline{H}_2CH_2$—) 5.11 (1H, s,$C\underline{H}$ at 4 position of dihydropyridine) 5.89 (1H,s,NH) 7.10–7.40 (11H,m,$C\underline{H}$ at 2,4,5,6 positions of phenyl ring, $C\underline{H}$ at 4,5 positions of imidazole and phenyl hydrogens of ester function) 7.78 (1H,dd,$C\underline{H}$ at 2 position of imidazole) MS: m/z 514 M⁺;

1,4-dihydro-2,6-dimethyl-4-[2-(1H-imidazol-1-yl)phenyl]-3,5-pyridinedicarboxylic acid, ethyl methyl ester;

1,4-dihydro-2,6-dimethyl-4-[2-(1H-imidazol-1-yl)phenyl]-3,5-pyridinedicarboxylic acid, methyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, isopropyl methyl ester;

1,4-dihydro-2,6-dimethyl-4-[3-(1H-imidazol-1-yl)phenyl]-3,5-pyridinedicarboxylic acid, ethyl isopropyl ester;

1,4-dihydro-2,6-dimethyl-4-[3-(1H-imidazol-1-yl)phenyl]-3,5-pyridinedicarboxylic acid, methyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, isopropyl methyl ester;

1,4-dihydro-2,6-dimethyl-4-[3-(1H-imidazol-1-yl)phenyl]-3,5-pyridinedicarboxylic acid, methyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, ethyl 2-[methyl(phenylmethyl)amino] ethyl ester;

1,4-dihydro-2,6-dimethyl-4-[3-(2-(1H-imidazol-1-yl)phenyl]- 3,5-pyridinedicarboxylic acid, ethyl methyl ester;

1,4-dihydro-2,6-dimethyl-4-[3-(2-(1H-imidazol-1-yl)phenyl]-3,5-pyridinedicarboxylic acid, methyl 2-[methyl(phenylmethyl)amino] ethyl ester; and 1,4-dihydro-2,6-dimethyl-4-[3-(1H-imidazol-1-yl)phenyl]-3,5-pyridinedicarboxylic acid, 5-amide 3-ethyl ester;

1,4-dihydro-2,6-dimethyl-4-[3-(1H-imidazol-1-yl)phenyl]-3,5-pyridinedicarboxylic acid, methyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, ethyl 2-[methyl(phenylmethyl)amino] ethyl ester.

EXAMPLE 3

A mixture of 2 g (4.76 mmol) of 1,4-dihydro-2,6-dimethyl- 4-[3-(1H-imidazol-1-yl)phenyl]-3,5-pyridinedicarboxylic acid, 2-cyanoethyl ethyl ester, 3 ml of 2N NaOH and 30 ml of ethanol was stirred for 12 hours at room temperature.

The mixture was diluted with water (40 ml) and extracted with ethyl acetate. The aqueous phase was acidified to pH=6 with 1N HCl.

The precipitate was collected, washed with water and dried under vacuum, giving 0.87 g (50%) of 1,4-dihydro-2, 6-dimethyl-4-[3-(1H-imidazol-1-yl)phenyl]- 3,5-pyridinedicarboxylic acid, ethyl ester (monohydrate), m.p. 117°–121° C. dec.

Elemental analysis: Calculated for $C_{20}H_{23}N_3O_5$: C 62.32; H 6.01; N 10.90 Found: C 62.12; H 6.07; N 10.85

T.L.C.: eluant $CHCl_3/CH_3OH=9/1$, $R_f=0.31$

N.M.R. (DMSO) δ p.p.m.: 1.10 (3H,t,$CH_2C\underline{H}_3$) 2.22 (6H,s,2 =C—$C\underline{H}_3$) 4.02 (2H,q,$CO_2C\underline{H}_2CH_3$) 4.92 (1H,s,$C\underline{H}$ at 4 position of dihydropyridine) 7.0–7.60 (6H, m,$C\underline{H}$ at 2,4,5,6 positions of phenyl ring and $C\underline{H}$ at 4,5 positions of imidazole) 8.05 (1H,dd,$C\underline{H}$ at 2 position of imidazole) 8.75 (1H,s,N$\underline{H}$);

By proceeding analogously the following compounds may be prepared:

1,4-dihydro-2,6-dimethyl-4-[3-(1H-imidazol-1-yl)phenyl]-3,5-pyridinedicarboxylic acid, ethyl ester; and 1,4-dihydro-2,6-dimethyl-4-[3-(1H-imidazol-1-yl)ethenyl)phenyl]- 3,5-pyridinedicarboxylic acid, ethyl ester.

EXAMPLE 4

A mixture of 1.2 g (0.0065 mol) of 3-(3-pyridyl)benzaldehyde, 1.7 g (0.0131 mol) of ethyl acetoacetate and 1.52 ml of 30% ammonium hydroxide in 10 ml of absolute ethanol was stirred under reflux for 4 hours and at room temperature for two days. The mixture was poured into ice-water and the aqueous solution was extracted with methylene chloride; the organic layers were put together, washed with water, dried over $CaCl_2$ and evaporated to dryness under vacuum. The residue was purified over flash silica-gel column n-hexane-:ethyl acetate= 1:1), giving a solid, which was crystallized from ethyl acetate. The precipitate was filtered off, affording 1.5 g (57%) of 1,4-dihydro-2,6-dimethyl-4-[3-(3-pyridyl)phenyl]- 3,5-pyridinedicarboxylic acid, diethyl ester, m.p. 183°–6°.

Elemental analysis: Found: C 70.99; H 6.46; N 6.84 Calculated for $C_{24}H_{26}N_2O_4$: C 70.92; H 6.45; N 6.89

TLC: eluant $CHCl_3/CH_3OH=190/10$ Rf=0.48

NMR ($CDCl_3$) δ p.p.m: 1.21 (6H, t, $CH_2C\underline{H}_3$) 2.35 (6H, s, =C—$C\underline{H}_3$) 4.10 (4H, q, $COOC\underline{H}_2CH_3$) 5.09 (1H, s, $C\underline{H}$ at 4 position of dihydropyridine) 5.81 (1H, s, N$\underline{H}$) 7.20–7.45 (4H, m, $C\underline{H}$ at 4, 5, 6 positions of phenyl ring and $C\underline{H}$ at 5 position of pyridine) 7.51 (1H, dd, $C\underline{H}$ at 2 position of phenyl ring) 7.83 (1H, ddd, $C\underline{H}$ at 4 position of pyridine) 8.65 (1H, dd, $C\underline{H}$ at 6 position of pyridine) 8.80 (1H, d, $C\underline{H}$ at 2 position of pyridine).

By proceeding analogously the following compounds may be prepared:

1,4-dihydro-2,6-dimethyl-4-[3-(3-pyridyl)phenyl]- 3,5pyridinedicarboxylic acid, diisobutyl ester, m.p. 97°–8° C., Elemental analysis: Found: C 72.51; H 7.60; N 5.81 Calculated for $C_{28}H_{34}N_2O_4$: C 72.70; H 7.41; N 6.05

TLC: eluant $CH_3CO_2$ Et/n-hexane=1/1 Rf =0.2

NMR ($CDCl_3$) δ p.p.m: 0.86 and 0.90 (each 6H, 2 d, $CH(C\underline{H}_3)_2$) 1.90 (2H, m, $CH_2$—$C\underline{H}(CH_3)_2$) 2.35 (6H, s, =C—$C\underline{H}_3$) 3.85 (4H, d, $COOC\underline{H}_2$—) 5.15 (1H, s, $C\underline{H}$ at 4 position of dihydropyridine) 5.70 (1H, s, N$\underline{H}$) 7.20 –7.45 (4H, m, $C\underline{H}$ at 4,5,6 positions of phenyl ring and $C\underline{H}$ at 5 position of pyridine) 7.52 (1H, bs, $C\underline{H}$ at 2 position of phenyl ring) 7.81 (1H, ddd, $C\underline{H}$ at 4 position of pyridine) 8.56 (1H, dd, $C\underline{H}$ at 6 position of pyridine) 8.80 (1H, d, $C\underline{H}$ at 2 position of pyridine );

1,4-dihydro-2,6-diethyl-4-[3-(3-pyridyl)phenyl]-3,5-pyridinedicarboxylic acid, diethyl ester;

1,4-dihydro-2,6-dimethyl-4-[2-fluoro-3(3-pyridyl)phenyl]-3,5-pyridinedicarboxylic acid, diethyl ester;

1,4-dihydro-2,6-dimethyl-4-[3-(3-pyridyl)phenyl]- 3,5-pyridinedicarboxylic acid, isobutyl methyl ester:

1,4-dihydro-2,6-dimethyl-4-[3-(3-pyridyl)phenyl]- 3,5-pyridinedicarboxylic acid, ethyl ester;

1,4-dihydro-2,6-dimethyl-4-[3-(3-pyridyl)phenyl]- 3,5-pyridinedicarboxylic acid, 5-amide-3-ethyl ester;

1,4-dihydro-2,6-dimethyl-4-[4-(3-pyridyl)phenyl]- 3,5-pyridinedicarboxylic acid, ethyl ester;

1,4-dihydro-2,6-dimethyl-4-[3-(3 -pyridyl-methyl)phenyl]- 3,5-pyridinedicarboxylic acid, diethyl ester;

1,4-dihydro-2,6-dimethyl-4-[3-(3-pyridyl-methyl)phenyl]- 3,5-pyridinedicarboxylic acid, ethyl ester.

EXAMPLE 5

A mixture of 0.55 g (0.003 mol) of 3-(3-pyridyl)benzaldehyde, 0.75 g (0.003 mol) of 2-[methyl(phenylmethyl)amino]ethyl acetoacetate and 0.38 g (0.003 mol) of ethyl-3-aminocrotonate in 10 ml of absolute ethanol was stirred under reflux for 30 hours. After cooling, the mixture was poured into ice-water, and the aqueous solution was extracted three times with ethyl acetate. The organic layers were put together, dried over $Na_2SO_4$ and evaporated under vacuum. The crude product was purified twice over flash silica-gel column n-hexane:ethyl acetate=1:9; chloroform:methanol=97:3). The appropriate fractions were put together, evaporated to dryness, affording 0.16 g (10 %) of 1,4-dihydro-2,6-dimethyl-4-[3-(3-pyridyl)phenyl]-3 5-pyridinedicarboxylic acid ethyl 2-[methyl(phenylmethyl)amino]ethyl ester, as an oil.

Elemental analysis: Found: C 71.90; H 6.85; N 7.75 Calculated for $C_{32}H_{35}N_3O_4$: C 73.12; H 6.71; N 7.99

TLC: eluant $CHCl_3/CH_3OH$=95/5 Rf =0.5

NMR ($CDCl_3$) δ p.p.m: 1.21 (3 H, t, $CH_2\underline{CH_3}$) 2.16 (3 H, s, N($\underline{CH_3}$)($CH_2Ph$)) 2.35 (6 H, s, =C—$\underline{CH_3}$) 2.64 (2 H, t, $\underline{CH_2}N(CH_3)$ ($CH_2Ph$ )) 3.45 (2 H, s, N($CH_3$)($\underline{CH_2}Ph$)) 4.12 (2 H, q, $COO\underline{CH_2}CH_3$) 4.20 (2H, t, $COO\underline{CH_2}CH_2$—) 5.11 (1H, s, C$\underline{H}$ at 4 position of dihydropyridine) 5.98 (1H, s, N $\underline{H}$) 7.20–7.45 (9H, m, C$\underline{H}$ at 4,5,6 positions of phenyl ring, C$\underline{H}$ at 5 position of pyridine and phenyl hydrogens of ester function) 7.51 (1H, bs, C$\underline{H}$ at 2 position of phenyl ring) 7.80 (1H, ddd, C$\underline{H}$ at 4 position of pyridine) 8.54 (1H, dd, C$\underline{H}$ at 6 position of pyridine) 8.80 (1H, d, C$\underline{H}$ at 2 position of pyridine).

By proceeding analogously the following compounds may be prepared:

1,4-dihydro-2,6-diethyl-4-[3-(3-pyridyl)phenyl]-3,5-pyridinedicarboxylic acid, ethyl 2-[methyl(phenylmethyl)amino]ethyl ester;

1,4-dihydro-2,6-dimethyl-4-[3-(3-pyridyl)phenyl]-3,5-pyridinedicarboxylic acid, isobutyl 2-[methyl(phenylmethyl)amino] ethyl ester.

EXAMPLE 6

The compound 1,4-dihydro-2,6-dimethyl-4-[3-(1H-imidazol-1-yl)phenyl]-3,5-pyridinedicarboxylic acid, diethyl ester (0.1 g) was dissolved in isopropyl alcohol (2 ml) and treated with isopropanolic HCl. The solution was evaporated to dryness and the residue crystallized from ethylacetate/ ethanol (3:1) mixture. The salt 1,4-dihydro-2,6-dimethyl-4-[ 3-(1H-imidazol-1-yl)phenyl]-3,5-pyridinedicarboxylic acid, diethyl ester hydrochloride was obtained in quantitative yield, m.p. 235°–240° C. (dec.).

Elemental analysis: Found: C 61.12; H 6.16; N 9.56 Calculated for $C_{22}H_{26}N_3O_4Cl$: C 61.18; H 6.07; N 9.73.

For the chloride ion: Found: $Cl^-$ 8.21% Calculated for $C_{22}H_{26}N_3O_4Cl$: $Cl^+$ 8.23%.

EXAMPLE 7

Tablets, each weighing 150 mg and containing 50 mg of the active substance were manufactured as follows:
Composition (for 10,000 tablets)

1,4-dihydro-2,6-dimethyl-4-[3-(1H-imidazol-1-yl)phenyl]-3,5-pyridinedicarboxylic acid, diethyl ester 500 g Lactose 710 g Corn starch 237.5 g Talc powder 37.55 g Magnesium stearate 15 g 1,4-dihydro-2,6-dimethyl-4-[3-(1H-imidazol-1-yl)phenyl]-3,5-pyridinedicarboxylic acid, diethyl ester, lactose and a half of the corn starch were mixed; the mixture was then forced through a sieve of 0.5 mm openings.

Corn starch (18 g) was suspended in warm water (180 ml).

The resulting paste was used to granulate the powder. The granules were dried, comminuted on a sieve of sieve size 1.4 mm, then the remaining quantity of starch, talc and magnesium was added, carefully mixed, and processed into tablets using punches of 8 mm diameter.

EXAMPLE 8

Tablets, each weighing 150 mg and containing 50 mg of the active substance were manufactured as follows:
Composition (for 10,000 tablets)

1,4-dihydro-2,6-dimethyl-4-(3(3-pyridyl)phenyl)-3,5-pyridine dicarboxylic acid,diethyl ester 500 g Lactose 710 g Corn starch 237.5 g Talc powder 37.5 g Magnesium stearate 15 g 1,4-dihydro-2,6-dimethyl-4-(3(3-pyridyl)phenyl)-3,5-pyridine dicarboxylic acid, diethyl ester, lactose and a half of the corn starch were mixed; the mixture was then forced through a sieve of 0.5 mm openings.

Corn starch (18 g) was suspended in warm Water (180 ml).

The resulting paste was used to granulate the powder. The granules were dried, comminuted on a sieve of sieve size 1.4 mm, then the remaining quantity of starch, talc and magnesium was added, carefully mixed, and processed into tablets using punches of 8 mm diameter.

We claim:

1. A compound having the following formula (I)

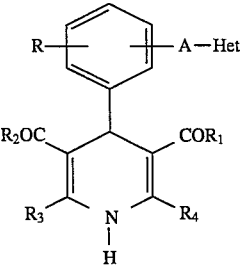

wherein

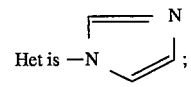

A represents —CH=CH—;

R is hydrogen, halogen, $C_1$–$C_3$ alkyl or $C_2$–$C_3$ alkoxy;

each of $R_3$ and $R_4$, which may be the same or different, is a $C_1$–$C_3$ alkyl group;

one of $R_1$ and $R_2$ is a group —OR' wherein R' is $C_1$–$C_6$ alkyl either unsubstituted or omega substituted by $C_1$–$C_3$ alkoxy and the other is, independently, (a) a group —OR' as defined hereabove, or (b) a group —OR$^{IV}$ wherein R$^{IV}$ is a substituent

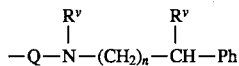

wherein Ph is a phenyl group either unsubstituted or substituted by one to three substituents selected from $C_1$–$C_3$ alkyl, $C_1$–$C_3$ alkoxy and halogen; Q is a $C_2$–$C_5$ alkylene radical; n is zero, 1 or 2; and each R$^V$ is, independently, hydrogen, $C_1$–$C_3$ alkyl or Ph, wherein Ph is as defined above;

or a pharmaceutically acceptable salt thereof.

2. A composition comprising a pharmaceutically acceptable carrier and an effective amount of a compound of claim 1 to inhibit Thromboxane $A_2$ synthase activity.

3. A composition comprising a pharmaceutically acceptable carrier and a compound of claim 1 in an amount effective to achieve synergy between TxA$_2$ inhibition and calcium antagonism.

4. A compound having the following formula (I)

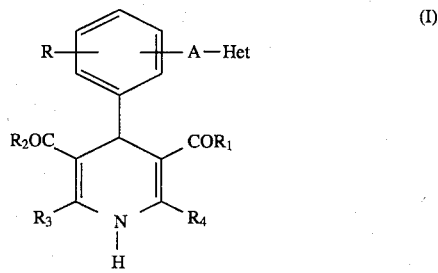

wherein

Het is

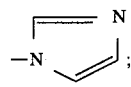

A represents a direct linkage at the meta position of the phenyl ring;

R is hydrogen, halogen, $C_1$–$C_3$ alkyl or $C_2$–$C_3$ alkoxy;

each of $R_3$ and $R_4$, which may be the same of different, is a $C_1$–$C_3$ alkyl group;

one of $R_1$ and $R_2$ is a group —OR' wherein R' is $C_1$–$C_6$ alkyl either unsubstituted or omega substituted by $C_1$–$C_3$ alkoxy and the other is, independently, (a) a group —OR' as defined hereabove; or (b) a group —OR$^{IV}$ wherein R$^{IV}$ is a substituent

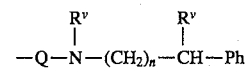

wherein Ph is a phenyl group either unsubstituted or substituted by one to three substituents chosen among $C_1$–$C_3$ alkyl, $C_1$–$C_3$ alkoxy and halogen; Q is a $C_2$–$C_5$ alkylene radical; n is zero, 1 or 2; and each R$^V$ is, independently, hydrogen, $C_1$–$C_3$ alkyl or Ph, wherein Ph is as defined above; or a pharmaceutically acceptable salt thereof.

5. A compound of the formula (I), according to claim 4, wherein R is hydrogen, $R_3$ and $R_4$ are both methyl groups or both ethyl groups, and each of $R_1$ and $R_2$, which may be the same or different, is a group —OR' wherein R' is unsubstituted $C_1$–$C_6$ alkyl, or a pharmaceutically acceptable salt thereof.

6. A compound of formula (I), according to claim 4, wherein:

R is hydrogen;

$R_3$ and $R_4$ are both methyl groups or both ethyl groups;

one of $R_1$ and $R_2$ is a group —OR' wherein R' is unsubstituted $C_1$–$C_6$ alkyl and the other is a group —OR$^{IV}$ as defined in claim 4.

7. A compound of formula (I), according to claim 4, which is 1,4-dihydro-2,6-dimethyl-4-[3-(1H-imidazol-1-yl)-phenyl]-3,5-pyridinedicarboxylic acid diethyl ester, or a pharmaceutically acceptable salt thereof.

8. A compound of formula (I), according to claim 4, selected from the group consisting of:

1,4-dihydro-2,6-dimethyl-4-[3-(1H-imidazol-1-yl)phenyl]-3,5-pyridinedicarboxylic acid, dimethyl ester;

1,4-dihydro-2,6-dimethyl-4-[3-(1H-imidazol-1-yl)phenyl]-3,5-pyridinedicarboxylic acid, ethyl methyl ester;

1,4-dihydro-2,6-dimethyl-4-[3-(1H-imidazol-1-yl)phenyl]-3,5-pyridinedicarboxylic acid, diethyl ester;

1,4-dihydro-2,6-dimethyl-4-[3-(1H-imidazol-1-yl)phenyl]-3,5-pyridinedicarboxylic acid, isopropyl methyl ester;

1,4-dihydro-2,6-dimethyl-4-[3-(1H-imidazol-1-yl)phenyl]-3,5-pyridinedicarboxylic acid, ethyl isopropyl ester;

1,4-dihydro-2,6-dimethyl-4-[3-(1H-imidazol-1-yl)phenyl]-3,5-pyridinedicarboxylic acid, methyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, ethyl 2-[methyl(phenylmethyl)amino] ethyl ester;

1,4-dihydro-2,6-dimethyl-4-[3-(1H-imidazol-1-yl)phenyl]-3,5-pyridinedicarboxylic acid, ethyl ester;

1,4-dihydro-2,6-dimethyl-4-[3-(1H-imidazol-1-yl)phenyl]-3,5-pyridinedicarboxylic acid, 5-amide 3-ethyl ester;

and the pharmaceutically acceptable salts thereof.

9. A composition comprising a pharmaceutically acceptable carrier and an effective amount of a compound of claim 4 to inhibit thromboxane $A_2$ synthase activity.

10. A composition comprising a pharmaceutically acceptable carrier and a compound of claim 4 in an amount effective to achieve synergy between TxA$_2$ inhibition and calcium antagonism.

* * * * *

UNITED STATES PATENT AND TRADEMARK OFFICE
CERTIFICATE OF CORRECTION

PATENT NO. : 5,514,693
DATED : May 7, 1996
INVENTOR(S) : Paolo COZZI, et al.

It is certified that error appears in the above-indentified patent and that said Letters Patent is hereby corrected as shown below:

On the title page, in Item [75], the third inventor's name should read:

--Maria Menichincheri--

Signed and Sealed this

Thirteenth Day of August, 1996

Attest:

BRUCE LEHMAN

*Attesting Officer*    *Commissioner of Patents and Trademarks*